(12) United States Patent
Bjåstad (10) Patent No.: US 11,521,335 B2
(45) Date of Patent: Dec. 6, 2022

(54) METHOD AND SYSTEM FOR COHERENT COMPOUNDING MOTION DETECTION USING CHANNEL COHERENCY AND TRANSMIT COHERENCY

(71) Applicant: GE Precision Healthcare LLC, Wauwatosa, WI (US)

(72) Inventor: Tore Bjåstad, Molde (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 494 days.

(21) Appl. No.: 16/674,130

(22) Filed: Nov. 5, 2019

(65) Prior Publication Data

US 2021/0134027 A1 May 6, 2021

(51) Int. Cl.
*G06K 9/00* (2022.01)
*G06T 11/00* (2006.01)
*G06T 7/246* (2017.01)
*G06T 7/00* (2017.01)
*A61B 8/08* (2006.01)

(52) U.S. Cl.
CPC .......... *G06T 11/005* (2013.01); *A61B 8/0833* (2013.01); *A61B 8/5253* (2013.01); *A61B 8/5276* (2013.01); *G06T 7/0016* (2013.01); *G06T 7/248* (2017.01); *G06T 2207/10132* (2013.01); *G06T 2207/20224* (2013.01); *G06T 2207/30048* (2013.01); *G06T 2207/30101* (2013.01)

(58) Field of Classification Search
CPC .................................................. G06T 11/005
See application file for complete search history.

(56) References Cited

U.S. PATENT DOCUMENTS 5,230,346 A * 7/1993 Leuchter .............. A61B 5/4088
600/544
6,769,769 B2 * 8/2004 Podoleanu ........... A61B 3/1025
356/497

(Continued)

OTHER PUBLICATIONS http://folk.ntnu.no/stoylen/strainrate/Basic_ultrasound, Basic ultrasound for clinicians, Jun. 2016 [accessed Feb. 5, 2020].

(Continued)

*Primary Examiner* — Oneal R Mistry
(74) *Attorney, Agent, or Firm* — McAndrews, Held & Malloy, Ltd.; Jacob Groethe; David Bates (57) ABSTRACT

The disclosure provides for a method for generating an ultrasound image that includes transmitting, by a plurality of transmitters in a transducer, at least two transmit beams at different angles, where at least parts of the transmit beams cover an overlapping region, and receiving, by a plurality of sensors of the transducer, reflected signals of the transmit beams. The method further comprises calculating channel coherence for the received signals to produce one or more channel coherence images, and calculating transmit coherence for the received signals to produce one or more transmit coherence images. The information from at least one of the channel coherence images and at least one of the transmit coherence images are combined to identify moving objects. The received signals from different transmits in overlapping regions are then processed to produce a final image that is compensated for the moving objects.

20 Claims, 9 Drawing Sheets

(56) References Cited

U.S. PATENT DOCUMENTS

| | | | | |
|---|---|---|---|---|
| 2012/0310081 A1* | 12/2012 | Adler | .................. | A61B 5/0046 |
| | | | | 600/427 |
| 2015/0342567 A1* | 12/2015 | Ustuner | .............. | A61B 8/5207 |
| | | | | 600/447 |
| 2015/0359512 A1* | 12/2015 | Boctor | ............... | G01S 15/8997 |
| | | | | 600/447 |
| 2017/0011499 A1* | 1/2017 | Reinhardt | ............... | G01S 17/18 |
| 2020/0163650 A1* | 5/2020 | Kruger | ................ | A61B 5/6832 |

OTHER PUBLICATIONS http://folk.ntnu.no/stoylen/strainrate/Basic_Doppler_ultrasound, Basic Doppler ultrasound for clinicians, Nov. 2018 [accessed Feb. 5, 2020].

New beamforming strategy for improved ultrasound imaging : application to biological tissues nonlinear imaging—Scientific Figure on ResearchGate. Available from: https://www.researchgate.net/figure/Beamforming-in-reception-used-in-ultrasound-imaging-scanners-The-time-delays-applied_fig5_281659456 Nov. 2014, [accessed Feb. 5, 2020].

* cited by examiner

METHOD AND SYSTEM FOR COHERENT COMPOUNDING MOTION DETECTION USING CHANNEL COHERENCY AND TRANSMIT COHERENCY

FIELD

Certain embodiments relate to ultrasound imaging. More specifically, certain embodiments relate to a method and system providing coherent compounding motion detection using channel coherency and transmit coherency.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

During ultrasound-based imaging of a patient, there may be times when an image of the patient is degraded. Accordingly, there are many efforts to provide an accurate and clear image.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for coherent compounding motion detection using channel coherency and transmit coherency, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for an exemplary ultrasound system that is operable to provide coherent compounding motion detection using channel coherency and transmit coherency. Various embodiments have the technical effect of improving an ultrasound image by accurately determining whether a pixel in an ultrasound image suffers from phase cancellation due to motion.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
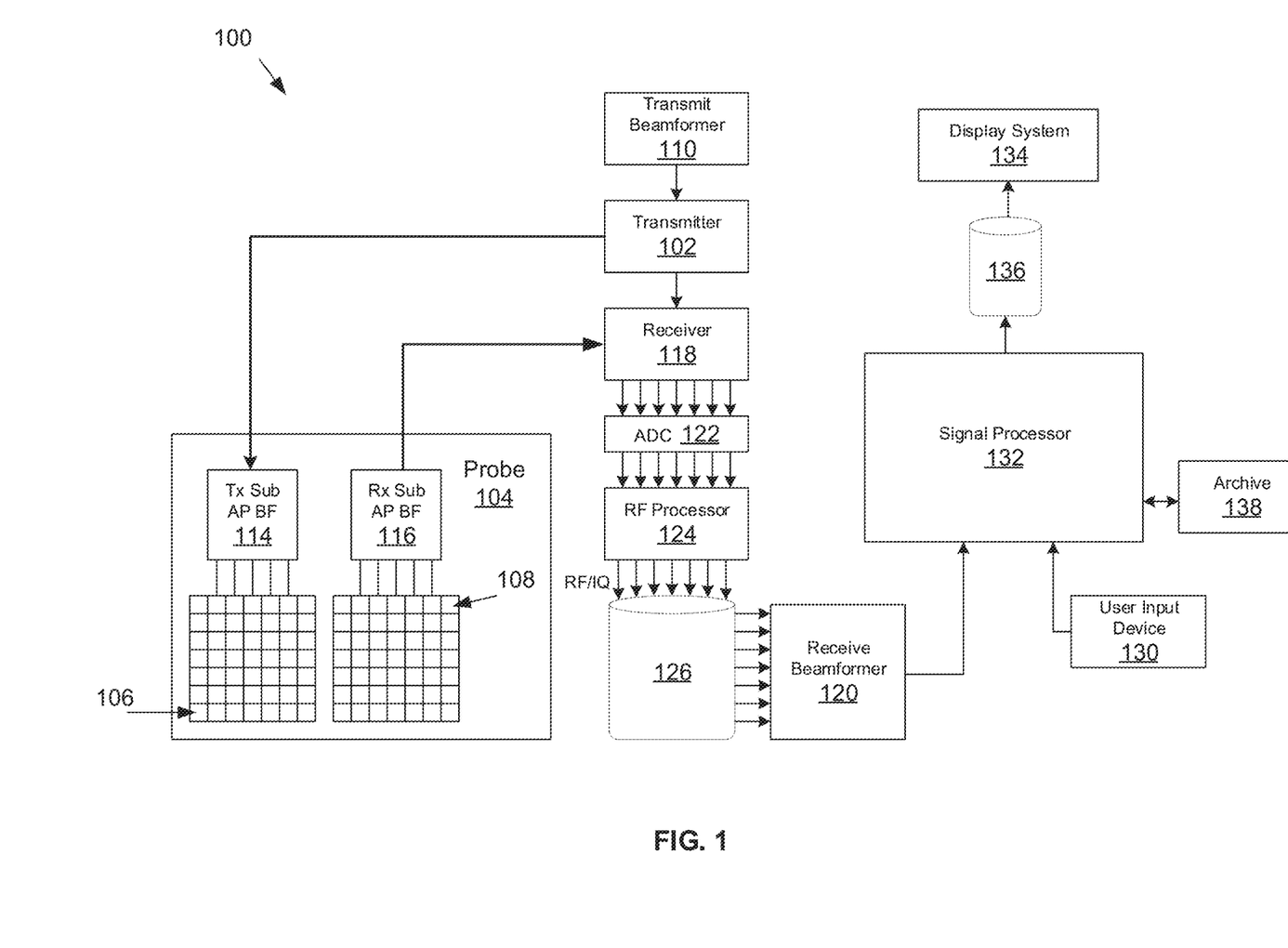
FIG. 1 is a block diagram of an exemplary ultrasound system that is operable to provide coherent compounding motion detection using channel coherency and transmit coherency, in accordance with various embodiments.

FIG. 1 is a block diagram of an exemplary ultrasound system that is operable to provide coherent compounding motion detection using channel coherency and transmit coherency, in accordance with various embodiments. Referring to FIG. 1, there is shown a block diagram of an exemplary ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF data, which may be, for example, I/Q signal data, real valued RF data, etc., may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

Accordingly, various embodiments may have, for example, the RF processor 124 process real valued RF data, or any other equivalent representation of the data, with an appropriate RF buffer 126.

The receive beamformer 120 may comprise suitable logic, circuitry, interfaces and/or code that may be operable to perform digital beamforming processing to, for example, sum delayed, phase shifted, and/or weighted channel signals received from RF processor 124 via the RF/IQ buffer 126 and output a beam summed signal. The delayed and/or phase shifted and weighted channel data may be summed to form a scan line output from the receive beamformer 120, where the scan line may be, for example, the complex valued or non-complex valued. The specific delay for a channel may be provided, for example, by the RF processor 124 or any other processor configured to perform the task. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may be capable of receiving input information from a user input device 130 and/or archive 138, generating an output displayable by a display system 134, and manipulating the output in response to input information from a user input device 130, among other things. The signal processor 132 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The display system 134 may be any device capable of communicating visual information to a user. For example, a display system 134 may include a liquid crystal display, a light emitting diode display, and/or any suitable display or displays. The display system 134 can be operable to present ultrasound images and/or any suitable information. For example, the ultrasound images presented at the display system 134 may include labels, tracking identifiers, and or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound image data, labeled ultrasound images, identification instructions, segmentation instructions, labeling instructions, and tracking instructions, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display. Furthermore, while the ultrasound system 100 was described to comprise an RF processor 124 and a signal processor 132, various embodiments of the disclosure may use only one processor. Various embodiments may refer to each of the RF processor 124 and the signal processor 132 as a processor. Furthermore, there may be other processors to additionally perform the tasks described as being performed by the RF processor 124 and the signal processor 132, and all of these processors may be referred to as a "processor" for ease of description.

Figure 2:
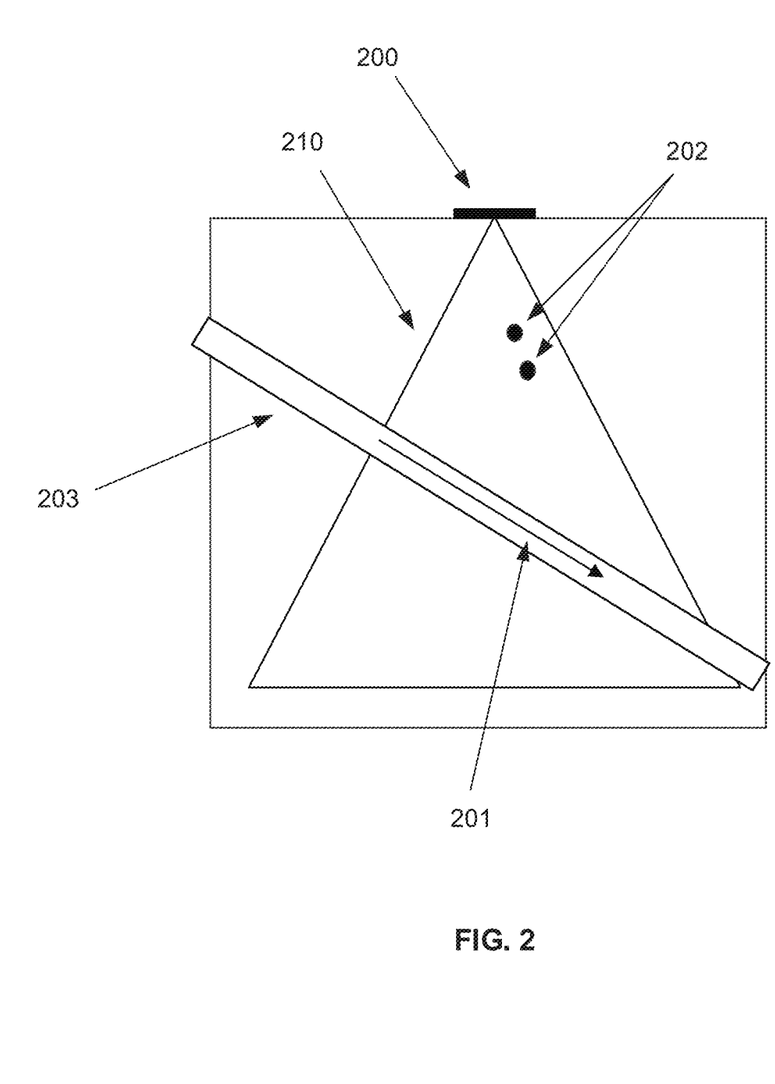
FIG. 2 is a diagram of an experimental ultrasound contrast imaging setup, in accordance with various embodiments.

FIG. 2 is a diagram of an experimental ultrasound contrast imaging setup, in accordance with various embodiments. Referring to FIG. 2 there is shown the ultrasound image probe 200, which may be similar to the ultrasound probe 104 of the ultrasound system 100. The ultrasound probe 200 may have an imaging section 210 where there is a tube 203 with a flowing contrast agent 201. Within the imaging section there are also a multitude of medium intensity stationary scatterers (not shown) and strong stationary point scatters 202.

A channel coherence image may be generated, for example, in the receive beamformer 120 (FIG. 1). A transmit coherence image may be generated, for example, either in the signal processor 132 (FIG. 1) or the receive beamformer 120, depending on how coherent compounding is implemented. However, as technology advances with graphics processing and software beamforming, the borders between beamforming and signal processing is getting more blurred.

For coherent compounding, it may also be assumed that the compounding is done on scan line data after the channel summation done in the beamforming process, however embodiments where the coherent compounding is done on channel data level is also possible. The exemplary embodiments also assume coherent compounding using focused transmits, but any other form of coherent compounding may also be used.

When generating an ultrasound image, channel coherency and transmit coherency methods may be used to provide better ultrasound images. Channel coherency methods may measure the alignment of the signals over all or parts of the channels after classical beamforming delays have been applied. Typically, these methods may ignore, partly or fully, the amplitude of the incoming echoes at each channel. Such methods may, among other things, output very low values for echoes arriving off axis from the intended beamforming direction, allowing them to be effective in suppressing sidelobe artifacts (simply referred to as "sidelobes") in ultrasound images. The output image from applying a coherency method may then either be used individually or combined with images from other types of beamforming such as, for example, Delay-And-Sum.

Transmit coherency methods may be similar to the channel coherency method. They can be applied, for example, in the cases where coherent compounding methods are in use. Coherent compounding methods are methods where data from several transmits are combined in the image reconstruction process. The difference from channel coherency methods is that the transmit coherency methods measure the alignment of data from different transmit events, rather than the alignment between data at different channels from the same transmit event. The data type where the alignment is measured may typically be scan line data (after summing the delayed channel data from parts of or all of the channels), but it can also be channel data.

When viewed at a high level and restricting channel and transmit coherency to be, for example, either high or low, a reconstructed pixel in an ultrasound image may represent one of four possible cases. The first case is when channel coherency is low and the transmit coherency is low. This may occur, for example, when the data used to reconstruct a pixel is noise or from off-axis scatterers (sidelobe data). The second case is when the channel coherency is low and transmit coherency is high. This case is not very likely, but may occur, for example, when the data used to reconstruct a pixel is from off-axis scatterers (sidelobe data) and where motion of the scatterer counters phase shifts between the combined transmits caused by off axis scatterers.

The third case is when channel coherency is high and transmit coherency is low. Generally, this may happen when the scatterer imaged in the reconstructed pixel is moving. This motion may cause the coherently combined transmits to be out of phase and causes a deterioration of the quality of the coherent compounding. Compensating for the motion when reconstructing the pixel (or region) may result in better final ultrasound image. The fourth case is when the channel coherency is high and the transmit coherency is high. This case indicates good quality echo data from stationary scatterers.

The third case may be a case when joint usage of channel and transmit coherencies is of interest. It is known from literature that when doing coherent compounding in a pixel where the data has a large amount of signal from an off-axis scatterer (sidelobe data), the data from the different combined transmits will be phase shifted compared to each other. If there is compensation for this phase shift before summation of the transmit data, the sidelobes may be reconstructed/amplified, something that is not desired. It is thus not possible to determine whether this phase shift is from motion or because of a strong off-axis scatterer. However, high channel coherency may be an indication that there is not a strong off-axis scatterer, hence, the low transmit coherency in this pixel may likely be caused by motion.

Accordingly, knowing that the pixel is imaging moving scatterers, phase and/or delay compensation may be applied to realign the transmit data before summing them, and thus achieve a better final ultrasound image. As explained previously, while various types of data can be used, there will be an assumption that complex baseband data is used for ease of reference. Accordingly, an example of phase compensation could be to estimate the average phase shift, ThetaAvg, between data from neighboring transmits used to reconstruct a pixel and then counter shifting the data of each transmit with TransmitIndex*ThetaAvg before summation of transmit data. The phase may be estimated by calculating the phase of the correlation between the complex valued data from the transmits used to reconstruct the pixel. Various embodiments of the disclosure is described with respect to FIGS. 3-9 for motion compensation for the third case.

Figure 3:
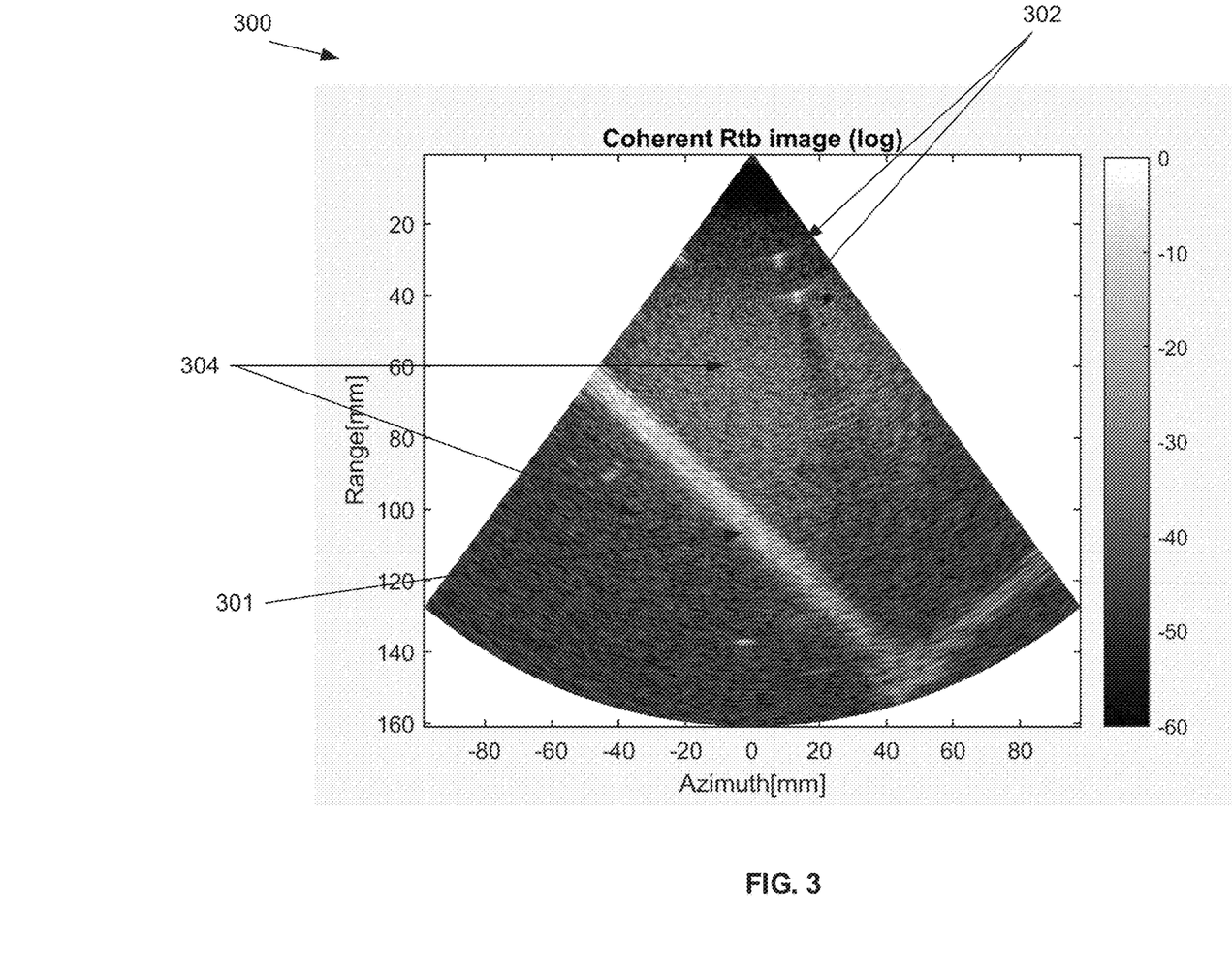
FIG. 3 is a display of an exemplary ultrasound image using coherent compounding, in accordance with various embodiments.

FIG. 3 is a display of an exemplary ultrasound image using coherent compounding, in accordance with various embodiments. Referring to FIG. 3, there is shown the ultrasound image 300 showing the resulting image after performing, for example, retrospective transmit beamforming (RTB) processing of the received echo data. That is, an image generated using coherent compounding of data from several focused transmit beams. The image is of the setup shown in FIG. 2. There is shown the contrast agent 301 and the stationary point scatterers 302. There is also shown the medium intensity scatterers 304 that may be seen as uniform speckle regions that are generally outside the tube 203, other than, for example, the bright point scatterers in the left bottom part of FIG. 3.

In the case of moving tissue such as, for example, the contrast agent 301, the pixel intensity may be reduced compared what the intensity would have been if the contrast agent was stationary. This may be because the data from the different transmits combined in the coherent compounding may be out of phase because of the motion. However, it may not be possible from the ultrasound image 300 alone to determine whether a pixel (or a region) displays lower intensity due to, for example, phase cancellation due to movement or whether the intensity is naturally lower because the imaged scatterer is weaker (reflects/scatters less ultrasound energy back towards the probe).

Figure 4:
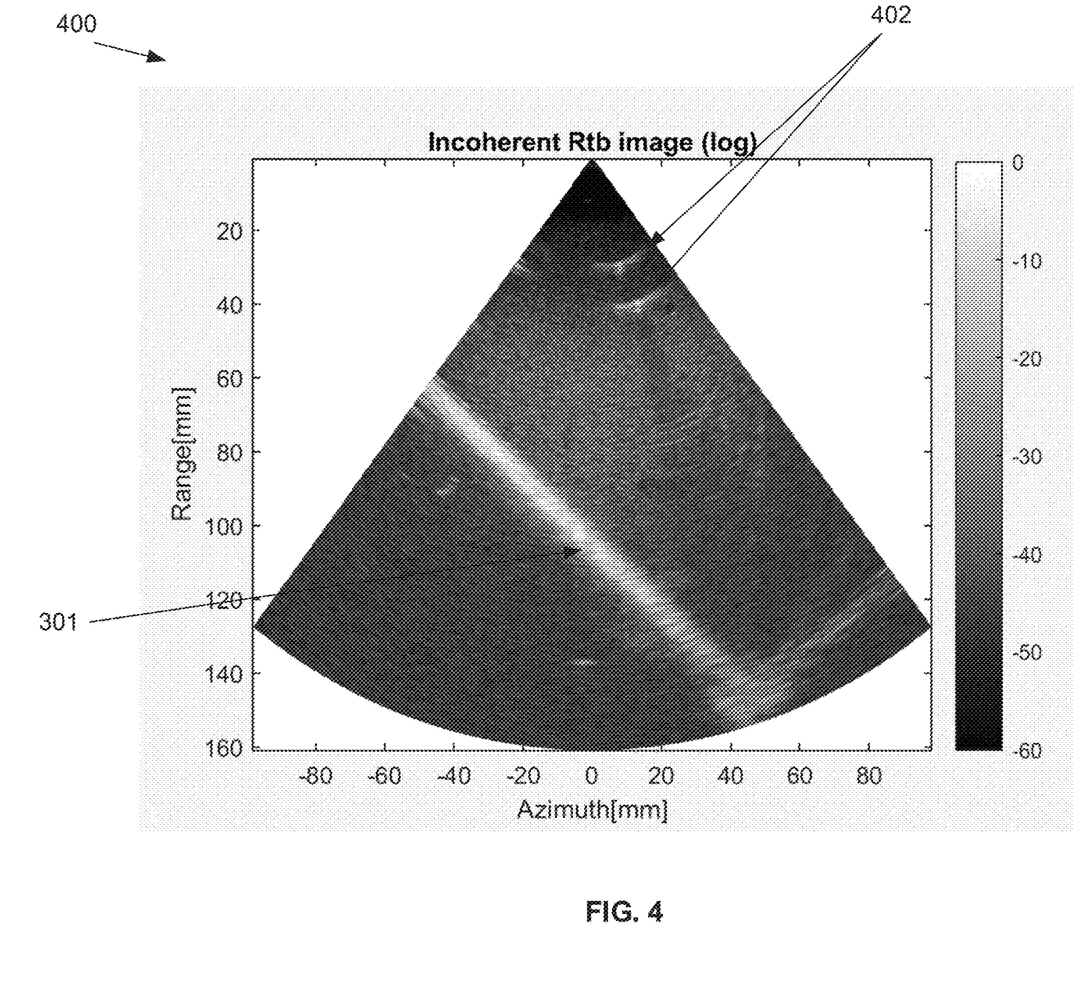
FIG. 4 is a display of an exemplary ultrasound image using incoherent compounding, in accordance with various embodiments, in accordance with various embodiments.

FIG. 4 is a display of an exemplary ultrasound image using incoherent compounding, in accordance with various embodiments. Referring to FIG. 4, there is shown the ultrasound image 400 showing the resulting image after performing, for example, incoherent retrospective transmit beamforming (iRTB) processing of the received echo data. That is, an image generated using incoherent compounding of data from several focused transmit beams. Incoherent compounding is when the absolute value of the data from the transmits are combined to reconstruct a pixel instead of the complex valued data. Coherent compounding combines the complex valued data. There is also shown the contrast agent 401 and the stationary point scatterers 402.

The resulting image using incoherent retrospective transmit beamforming is an image generated using incoherent compounding of data from several focused transmit beams. Incoherent compounding combines the absolute value of the data from the transmits to reconstruct a pixel instead of the complex valued data (which would be the case for coherent compounding). By using the absolute value, one avoids potential destructive interference when combining data from several transmits. Consequently, motion may not matter since the intensity of a pixel may be the same regardless of whether the tissue is moving or not.

The ultrasound image 400 may be immune to motion artifacts, however, a disadvantage may be that the sidelobes are too big. This can be seen by comparing the pixel intensity in the regions to the left/right of the point scatterers 302 and 402 in the coherent RTB image in FIG. 3 and the incoherent RTB image in FIG. 4, respectively. The intensity at the side regions of the scatterers 402 should be as low as possible. Accordingly, it can be seen that coherent RTB is better than incoherent RTB in this regard.

While an embodiment is described as using complex valued data (I/Q data), various embodiments may use real valued RF data, or any other equivalent representation of the data.

Figure 5:
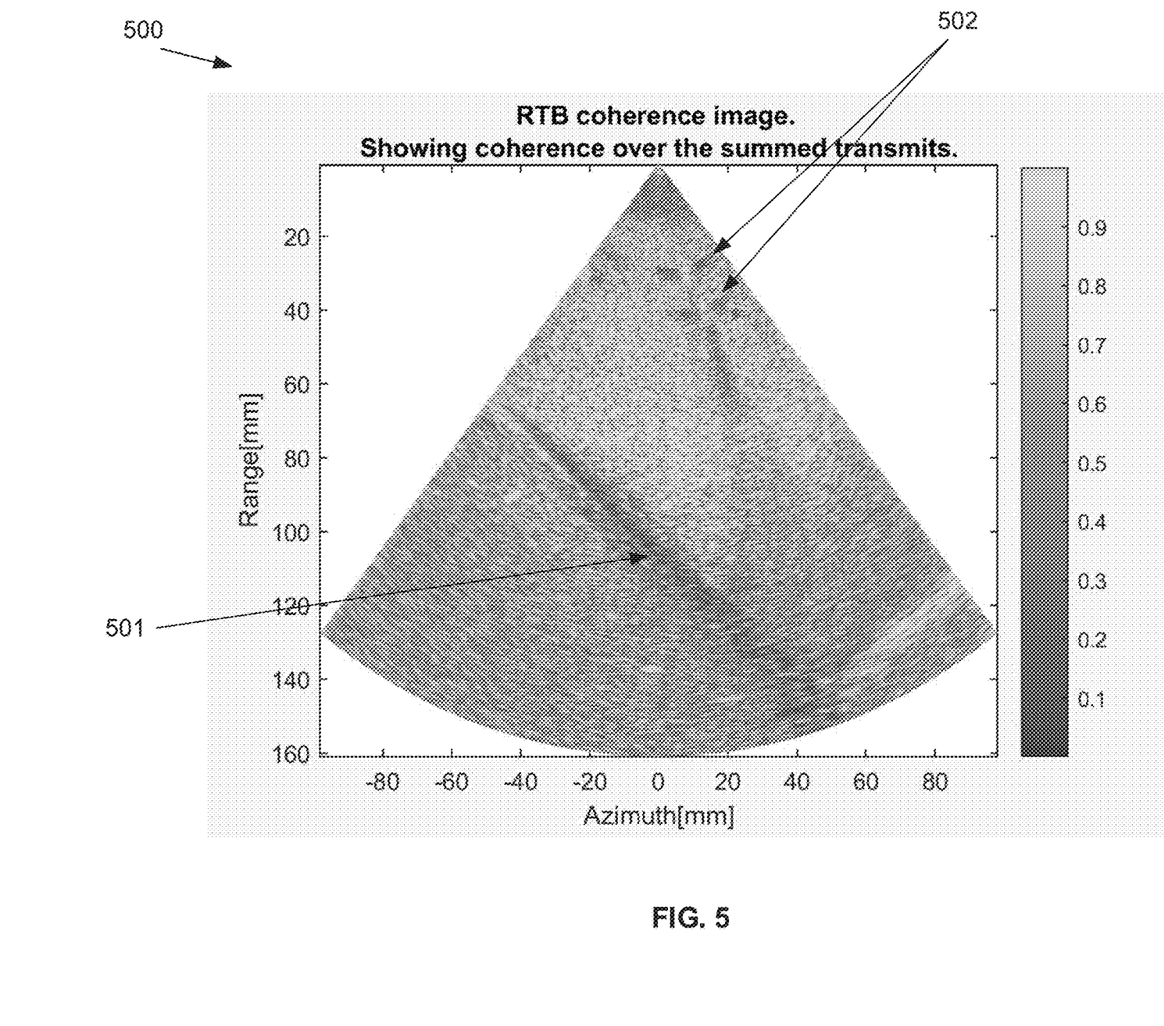
FIG. 5 is a display of an exemplary transmit coherence image, in accordance with various embodiments.

FIG. 5 is a display of an exemplary transmit coherence image, in accordance with various embodiments. Referring to FIG. 5, there is shown the transmit coherence image 500 showing a transmit coherence image (CFtx) generated after proper delay has been applied to all transmit data that is to be summed, but before the actual summation is done. There is also shown the contrast agent 501 and the stationary point scatterers 502.

Coherency of the data from the summed transmit may be examined by using, for example, a coherence factor (CF). For example, the transmit coherence value in the image might be calculated for each pixel in the image may be set to be abs(SumTransmitData/SumAbsTransmitData), where the sum is done over all transmits contributing to the pixel. It should be noted that "abs" is an absolute value operator, SumTransmitData is a sum of the data from the different transmits used in the coherent compounding, and SumAbsTransmitData is an absolute value of each of the respective transmit data before doing the summation in the coherent compounding. That is, an absolute value of each transmit data is used for the summation in the coherent compounding. Accordingly, dividing the coherent RTB image by the incoherent RTB image may be used to generate the transmit coherence image (CFtx) and may be referred to as the coherence factor process. Additionally, one of different coherence factors such as, for example, Generalized Coherence Factor, Phase Coherence Factor, Sign Coherence Factor, etc., may also be used in the process of determining channel/transmit coherence. As these processes are well know, these processes are not described.

The resulting transmit coherence image (CFtx) is shown in FIG. 5. As can be seen, the pixel intensity in the region with flowing contrast agent 501 is lower. However, this may also be the case for the sidelobe regions to the sides of the point scatterers 502.

It may still be difficult to differentiate between low intensity from sidelobes versus low intensity from motion.

Figure 6:
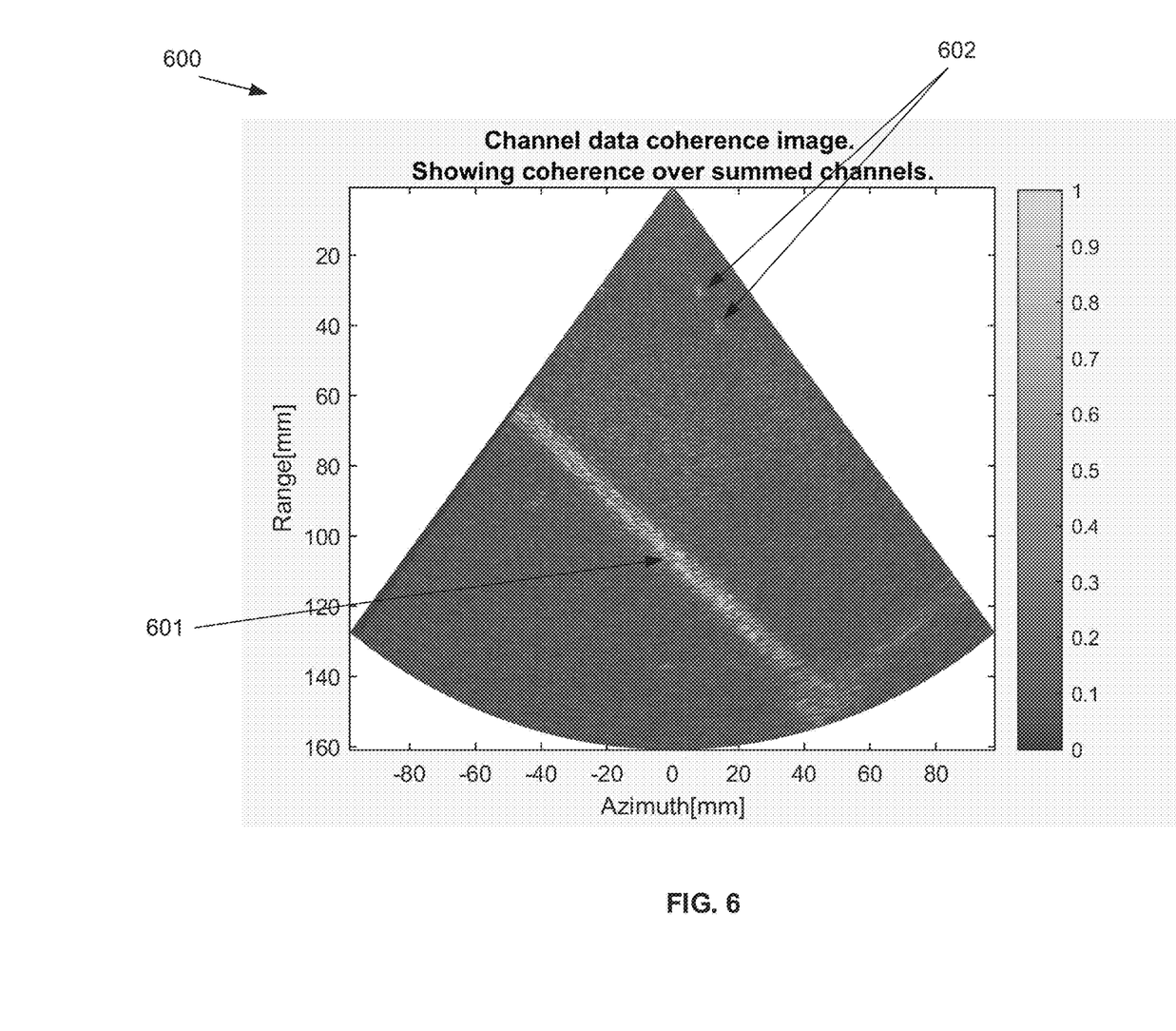
FIG. 6 is a display of an exemplary channel coherence image, in accordance with various embodiments.

FIG. 6 is a display of an exemplary channel coherence image, in accordance with various embodiments. Referring to FIG. 6, there is shown the channel coherence image 600 showing a channel coherence image (CFch) showing the coherency of the channel data. That is, channel coherence image (CFch) illustrates the data aligned over all channels after applying beamforming delays, and before summing them in the beamforming process. There is also shown the contrast agent 601 and the stationary point scatterers 602.

The channel coherence image 600 may be generated in a similar way as the transmit coherence image. For example, the channel coherence value in the image might be calculated as abs(SumChannelData/SumAbsChannelData), where the sum may be over all channels contributing to the reconstructed pixel. It should be noted that, as explained above, "abs" is an absolute value operator. SumChannelData is a sum of the channel data in the receive beamforming and SumAbsChannelData is an absolute value of each of the respective channel data before doing the summation of the channel data. That is, an absolute value of each channel data is used for the summation of the channel data. Since all data used in this coherence factor image is from a single transmit and not different transmits, the channel coherence image 600 is not affected by motion. Therefore, this image alone cannot detect motion. However, the channel coherence image (CFch) may get low values in a region affected by sidelobe transmission. This can be seen in FIG. 6. While there may be other causes of low channel coherency, sidelobes may be a likely cause.

It should be noted that various embodiments of the disclosure may use a different coherence measure such as, for example, Generalized Coherence Factor, Phase Coherence Factor, Sign Coherence Factor, etc. Accordingly, various embodiments may use different methods for generating both the channel coherence image and the transmit coherence image, as well as using a first method for generating the channel coherence image and a second method for generating the transmit coherence image.

Figure 7:
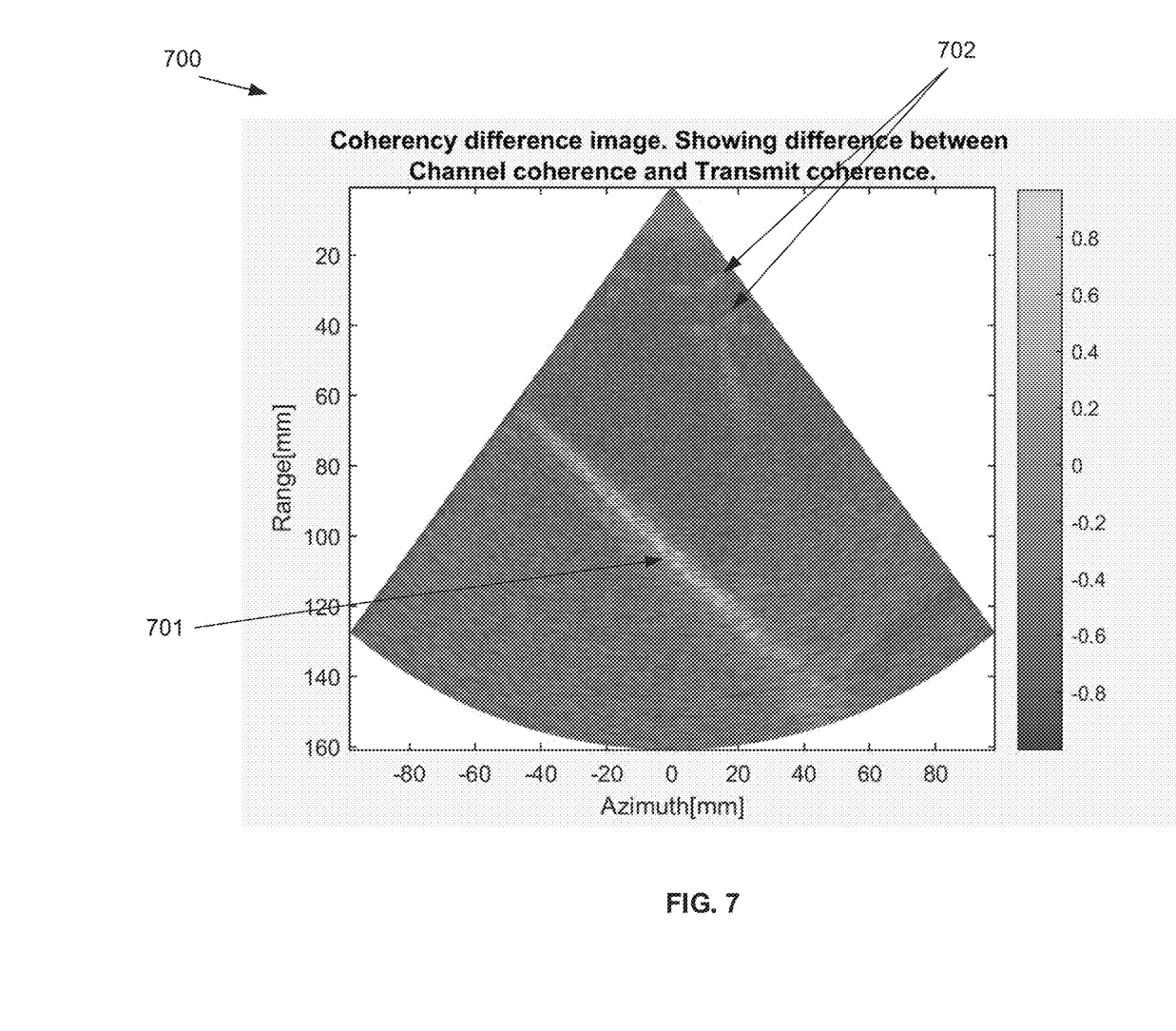
FIG. 7 is a display of an exemplary coherency difference image, in accordance with various embodiments.

FIG. 7 is a display of an exemplary coherency difference image, in accordance with various embodiments. Referring to FIG. 7, there is shown the ultrasound image 700 showing a difference of the channel coherence image (CFch) and the transmit coherence image (CFtx). There is also shown the contrast agent 701 and the stationary point scatterers 702.

One way of determining a region with motion may be to subtract the transmit coherence image (CFtx) from the channel coherence image (CFch):

$$CFdiff = CFch - CFtx \qquad \text{(Equation 1)}$$

The CFdiff value (difference value) may then be compared to a threshold, where a CFdiff value higher than the threshold may be considered to have motion. In other words, the CFdiff value is considered to be for a part of a moving object. This may be done, for example, on a pixel by pixel basis, or any other grouping of pixels.

Other embodiments may use, for example, the ratio between the transmit and channel coherence images.

Accordingly, it can be seen in FIG. 7 that pixels with moving tissue (contrast agent 701) have higher intensity than pixels at sides of the point scatterers 702. Accordingly, pixels inside the tube 203 of flowing contrast agent 701 may be an example of case 3 and pixels at the sides of the point scatterers 702 may an example of case 1 as sidelobes generally have low channel coherence and low transmit coherence, as categorized above with respect to FIG. 2.

Figure 8:
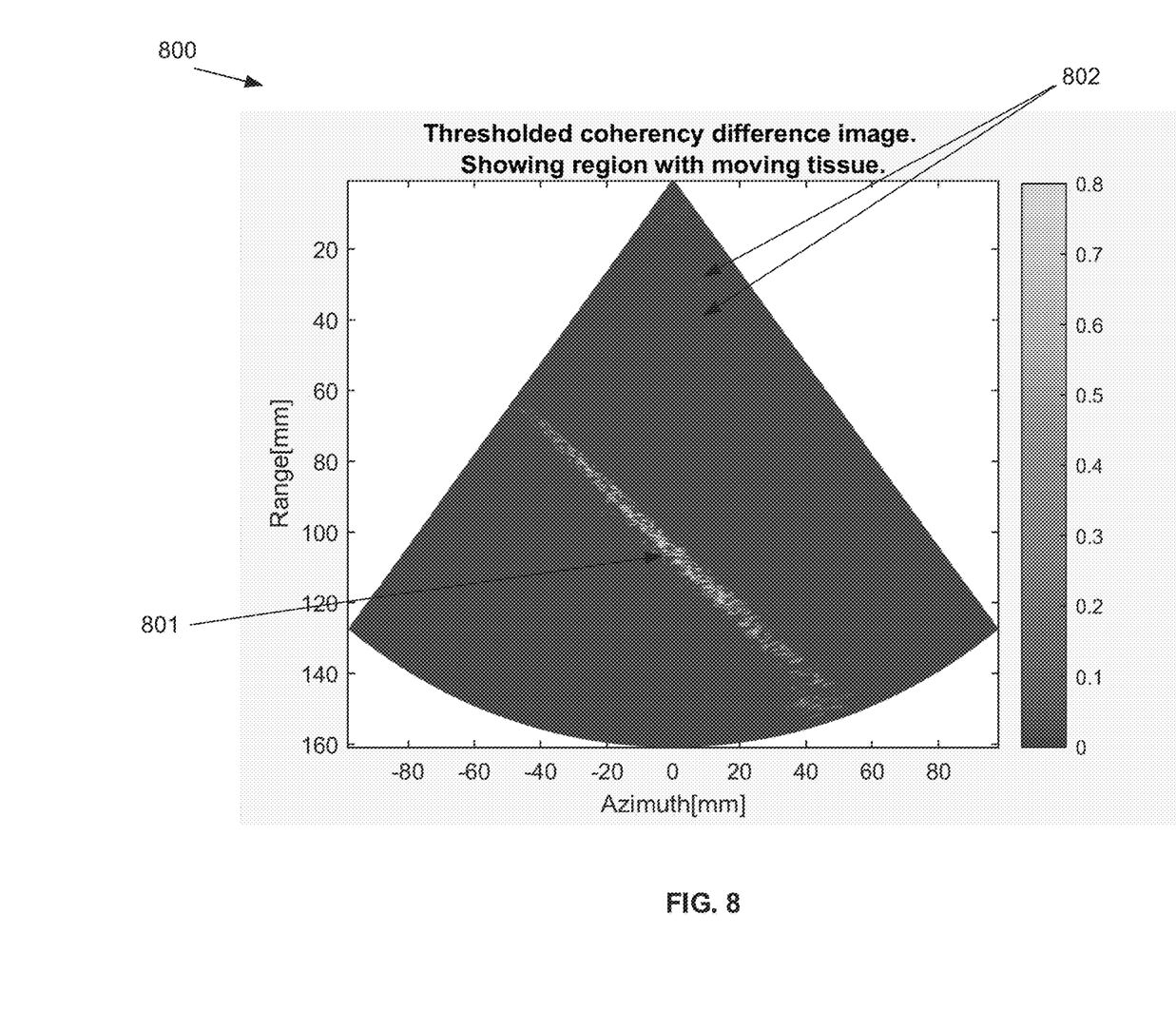
FIG. 8 is a display of the exemplary coherency difference image of FIG. 7 after processing to detect regions with moving tissues, in accordance with various embodiments.

FIG. 8 is a display of the exemplary coherency difference image of FIG. 7 after processing to detect regions with moving tissues, in accordance with various embodiments. Referring to FIG. 8, there is shown the ultrasound image 800 showing the thresholded coherency difference image. There is also shown the contrast agent 801 and the stationary point scatterers 802.

To generate the thresholded difference image, a threshold may be used to compare to CFdiff such that pixels (or regions) with CFdiff value higher than the threshold may be considered to be moving tissue. For example, in an example embodiment of the disclosure, the threshold may be zero (or some other value). Having identified the pixels with moving tissue, one could correct the phase and/or delay errors caused by motion in just these pixels.

Various embodiments may also use soft weighting of corrected image. For example, the pixel may be weighted, for example, by a floating point number. As an example, there may be two values of a pixel (or a region) where one is a motion compensated value Pm, and a non-compensated value P, where P may be the original value. Accordingly, an output pixel value Po (or region) may be shown as:

$$Po = Pm * CFdiff + (1 - CFdiff) * P \qquad \text{(Equation 2)}$$

Pm may also be, for example, the incoherent RTB image. Then the incoherent RTB image may be weighted according to a likelihood of moving tissue, given by CFdiff. This way one may get the motion resilience of incoherent RTB, and may avoid the high sidelobes.

Hard weighting may also be used, where the value of the motion compensated pixel value Pm is used or the non-compensated pixel value P.

As can be seen in FIG. 8, pixels in moving tissue (contrast agent 801) have higher intensity than pixels in sides of the point scatterers 802. Accordingly, it can be seen that further compensation may be made for the intensity loss in coherent compounding from the motion in the indicated region. This could, for example, be used for phase compensation in these pixels, or to use incoherent summation in these pixels, etc.

A soft mask using soft weighting may be used, for example, to weigh in the compensated pixels based on the CFdiff intensity.

Figure 9:
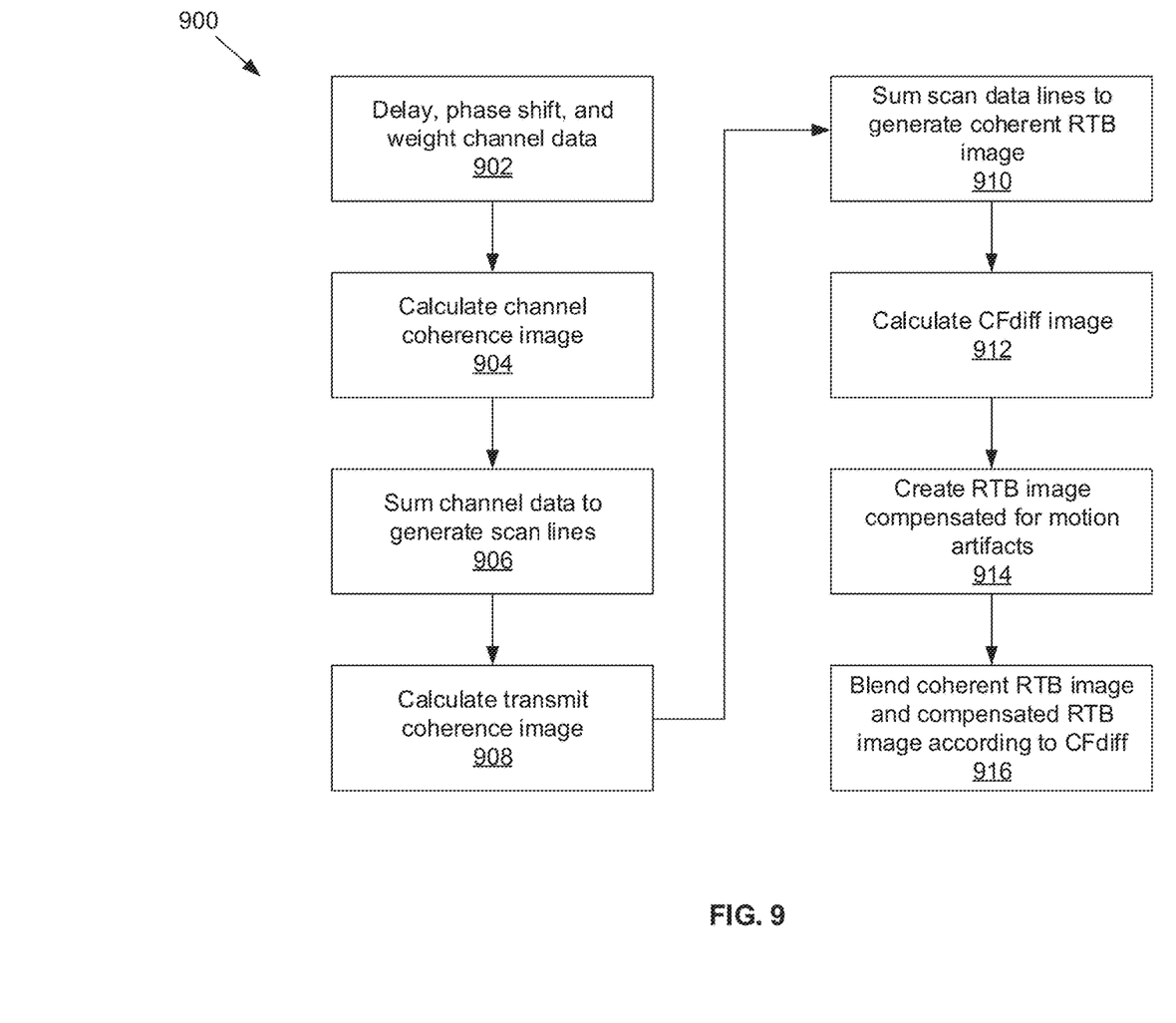
FIG. 9 is a flow chart illustrating exemplary steps that may be utilized for providing coherent compounding motion detection using channel coherency and transmit coherency, in accordance with various embodiments.

FIG. 9 is a flow chart illustrating exemplary steps that may be utilized for providing coherent compounding motion detection using channel coherency and transmit coherency, in accordance with various embodiments. Referring to FIG. 9, there is shown a flow diagram 900 with blocks 902 to 916.

In block 902 the channel data for each transmit event are delayed and/or phase shifted and weighted by, for example, the RF processor 124 and/or the receive beamformer 120. Both the delays for classical Delay-And-Sum (DAS) and the Retrospective Transmit Beamforming (RTB) (or any other coherent compounding technique) may be applied. The DAS delays/phases are applied to steer the scan lines in the appropriate directions for each transmit to perform RTB later in the processing. This may mean that scan lines are steered in the same direction for all the transmits that are to be combined in that scan line direction. The DAS delays/weights/phases may vary across the channels and range. The RTB delays/phases/weights may be, for example, constant over all channels, but may vary in range.

In block 904, the channel coherence image (CFch) may be generated by, for example, the receive beamformer 120. This can be done, for example, by calculating abs(SumChannelData/SumAbsChannelData), where the sum is done over all channels contributing to the reconstructed pixel along a scan line.

In block 906, the delayed and/or phase shifted and weighted channel data is summed to form the complex valued scan line output from the receive beamformer 120.

In block 908, the transmit coherence image, CFtx, is calculated by, for example, the signal processor 132. This can be done, for example, by calculating abs(SumTransmitData/SumAbsTransmitData) as discussed above, where TransmitData are the scan lines data from all the transmits that are to be combined to create a output pixel.

In block 910, the weighted, delayed and/or phase shifted scan line data from all the transmits that are to be combined to create each pixels are summed to form the complex valued coherent RTB image. This may be done, for example, by the signal processor 132.

In block 912, the difference image CFdiff between channel coherence image and transmit coherence image is generated by, for example, the signal processor 132. This could for example be generated as CFdiff=CFch−CFtx.

In block 914, a compensated RTB image is generated by, for example, the signal processor 132. This could be, for example, an image where the phase shift between all combined scan lines are calculated and compensated for. This would then compensate for both motion artifacts and reconstruct sidelobes. Alternatively it could be an incoherent RTB image, where the absolute values of the scan lines are combined instead of the complex values. This image would not be affected by motion, but would have high sidelobes.

In block 916, the compensated RTB image is blended with the coherent RTB image (uncompensated) by, for example, the signal processor 132. The value of CFdiff is used to determine which pixels are affected by motion, and thus should use the pixel value from the compensated RTB image instead of the uncompensated. Another method may use a soft weighting of the compensated RTB image such as, for example, Equation 2:

$$Po=Pm*CFdiff+(1-CFdiff)*P,$$

where Po is output image, Pm is compensated image, and P is the uncompensated image.

Other methods may also be used for determining Po. For example, rather than calculating both the full uncompensated and the full compensated images, the compensated pixels may be calculated where they are needed. Accordingly, the compensation may be for one or more pixels, an area in the image, or the entire image.

As can be seen, the disclosure provides for a method for generating an ultrasound image that comprises transmitting, by a plurality of transmitters in a transducer, at least two transmit beams at different angles, where at least parts of the transmit beams cover an overlapping region, and receiving, by a plurality of sensors of the transducer, reflected signals of the transmit beams.

Channel coherence for the received signals may be calculated for use in producing one or more channel coherence images, and transmit coherence calculated for the received signals for use in producing one or more transmit coherence images. The information from at least one of the channel coherence images and at least one of the transmit coherence images may be combined to identify moving objects. The received signals from different transmits in overlapping regions may be processed to produce a final image that is compensated for the moving objects.

Calculating the channel coherence may comprise performing upon the received signals one or more of the following: delaying, weighting, and phase shifting the received signals. Calculating the channel coherence may be performed with respective received signals at each sensor of the transducer. Calculating the transmit coherence may comprise using scan line data representing the overlapping region covered by the transmit beams, where the scan lines may be generated by one or more of processing, weighting, delaying, phase shifting, and summing the respective received signals for use in calculating transmit coherence.

The method further comprises calculating the channel coherence using coherence factor process comprising abs (SumChannelData/SumAbsChannelData), where "abs" is an operator for an absolute value, SumChannelData is a sum of channel data in the receive beamforming, and SumAbsChannelData is an absolute value of each of respective the channel data before doing the sum of the channel data. The method further provides calculating the transmit coherence using coherence factor process comprising abs(SumTransmitData/SumAbsTransmitData), where SumTransmitData is a sum of data from the different transmits used in coherent compounding, and SumAbsTransmitData is an absolute value of each of the respective transmit data before doing the sum in the coherent compounding.

Identifying the moving objects comprises generating a difference value (CFdiff) for a first portion P of an image by subtracting a corresponding first portion of the transmit coherence image (CFtx) from a corresponding first portion of the channel coherence image (CFch), and comparing the difference value (CFdiff) to a threshold. When the difference value is higher than the threshold, the first portion P of the image is considered to be a part of a moving object and set to be a compensated image Pm. When the difference value is not higher than the threshold, the first portion P of the image is not considered to be a part of a moving object and set to be a non-compensated image P. The first portion may be, for example, a pixel or a group of pixels.

The first portion Po may be generated, for example, using the equation: Po=Pm*CFdiff+(1−CFdiff)*P, where Pm is a compensated first portion, and P is the uncompensated first portion.

The channel coherence is calculated using one of the following processes: Generalized Coherence Factor, Phase Coherence Factor, or Sign Coherence Factor. The transmit coherence is calculated using one of the following processes: Generalized Coherence Factor, Phase Coherence Factor, or Sign Coherence Factor. Producing the one or more transmit coherence images may comprise using retrospect transmit beamforming.

The disclosure may also provide for a system 100 for generating an ultrasound image, where the system 100 may comprise a plurality of transmitters (transmit transducer elements) 106 in a transducer (probe) 104 configured to transmit at least two transmit beams at different angles, where at least parts of the transmit beams cover an overlapping region. The system 100 may also comprise a plurality of sensors (receive transducer elements) 108 of the transducer configured to receive reflected signals of the transmit beams. The system 100 may comprise one or more processors 124/120/132 configured to calculate channel coherence for the received signals to produce one or more channel coherence images and calculate transmit coherence for the received signals to produce one or more transmit coherence images The one or more processors 124/120/132 may be configured to combine information from at least one of the channel coherence images and at least one of the transmit coherence images to identify moving objects, and process the received signals from different transmits in overlapping regions to produce a final image compensated for the moving objects. The system 100 may also comprise a display 134 configured to display the final image.

The one or more processors 124/120/132 may be configured to calculate the channel coherence by using the received signals to which are performed one or more of the following: delaying, weighting, and phase shifting the received signals. The one or more processors 124/120/132 may be configured to calculate the channel coherence with respective received signals at each sensor of the transducer (probe) 104. The one or more processors 124/120/132 may be configured to calculate the transmit coherence using scan line data representing the overlapping region covered by the transmit beams, and the scan lines may be generated by one or more of processing, weighting, delaying, phase shifting, and summing the respective received signals for use in calculating transmit coherence.

The one or more processors 124/120/132 may be configured to calculate the channel coherence using coherence factor process comprising abs(SumChannelData/SumAbsChannelData), where "abs" is an operator for an absolute value, SumChannelData is a sum of channel data in the receive beamforming, and SumAbsChannelData is an absolute value of each of respective the channel data before doing the sum of the channel data. The one or more processors 124/120/132 may also calculate the transmit coherence using coherence factor process comprising abs(SumTransmitData/SumAbsTransmitData), where SumTransmitData is a sum of data from the different transmits used in coherent compounding, and SumAbsTransmitData is an absolute value of each of the respective transmit data before doing the sum in the coherent compounding.

The one or more processors 124/120/132 may be configured to identify the moving objects by generating a difference value (CFdiff) for a first portion P of an image by subtracting a corresponding first portion of the transmit coherence image (CFtx) from a corresponding first portion of the channel coherence image (CFch), and comparing the difference value to a threshold. When the difference value is higher than the threshold, the first portion P of the image may be considered to be a part of a moving object and set to be a compensated image Pm. When the difference value is not higher than the threshold, the first portion P of the image may not be considered to be a part of a moving object, and set to be a non-compensated image P.

The one or more processors 124/120/132 may be configured to generate the first portion Po using equation: Po=Pm*CFdiff+(1−CFdiff)*P, where Pm is a compensated first portion, and P is the uncompensated first portion. The one or more processors 124/120/132 may be configured to use retrospect transmit beamforming to produce the one or more transmit coherence images.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for facilitating interaction by an ultrasound operator.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What are claimed:

1. A method for generating an ultrasound image, comprising:
   transmitting, by a plurality of transmitters in a transducer, at least two transmit beams at different angles, wherein at least parts of the transmit beams cover an overlapping region;
   receiving, by a plurality of sensors of the transducer, reflected signals of the transmit beams;
   calculating channel coherence for the received signals to produce one or more channel coherence images;
   calculating transmit coherence for the received signals to produce one or more transmit coherence images;
   combining information from at least one of the channel coherence images and at least one of the transmit coherence images to identify moving objects; and
   processing the received signals from different transmits in overlapping regions to produce a final image compensated for the moving objects.

2. The method of claim 1, wherein calculating the channel coherence uses the received signals to which are performed one or more of the following: delaying, weighting, and phase shifting the received signals.

3. The method of claim 1, wherein calculating the channel coherence is performed with respective received signals at each sensor of the transducer.

4. The method of claim 1, wherein calculating the transmit coherence comprises using scan line data representing the overlapping region covered by the transmit beams.

5. The method of claim 4, wherein the scan lines are generated by one or more of processing, weighting, delaying, phase shifting, and summing the respective received signals for use in calculating transmit coherence.

6. The method of claim 1, wherein:
   the channel coherence is calculated using coherence factor process comprising abs(SumChannelData/SumAbsChannelData), where "abs" is an operator for an absolute value, SumChannelData is a sum of channel data in the receive beamforming, and SumAbsChannelData is an absolute value of each of respective the channel data before doing the sum of the channel data, and
   the transmit coherence is calculated using coherence factor process comprising abs(SumTransmitData/SumAbsTransmitData), where SumTransmitData is a sum of data from the different transmits used in coherent compounding, and SumAbsTransmitData is an absolute value of each of the respective transmit data before doing the sum in the coherent compounding.

7. The method of claim 1, wherein identifying the moving objects comprises:
   generating a difference value (CFdiff) for a first portion P of an image by subtracting a corresponding first portion of the transmit coherence image (CFtx) from a corresponding first portion of the channel coherence image (CFch); and
   comparing the difference value to a threshold,
   wherein when the difference value is higher than the threshold, the first portion P of the image is considered to be a part of a moving object and set to be a compensated image Pm, and
   wherein when the difference value is not higher than the threshold, the first portion P of the image is not considered to be a part of a moving object and set to be a non-compensated image P.

8. The method of claim 7, wherein the first portion is a pixel.

9. The method of claim 7, wherein the first portion Po is generated by equation: Po=Pm*CFdiff+(1−CFdiff)*P, where Pm is a compensated first portion, and P is the uncompensated first portion.

10. The method of claim 1, wherein the channel coherence is calculated using one of the following processes: Generalized Coherence Factor, Phase Coherence Factor, or Sign Coherence Factor.

11. The method of claim 1, wherein the transmit coherence is calculated using one of the following processes: Generalized Coherence Factor, Phase Coherence Factor, or Sign Coherence Factor.

12. The method of claim 1, wherein producing the one or more transmit coherence images comprises using retrospect transmit beamforming.

13. A system for generating an ultrasound image, comprising:
   a plurality of transmitters in a transducer configured to transmit at least two transmit beams at different angles, wherein at least parts of the transmit beams cover an overlapping region;
   a plurality of sensors of the transducer configured to receive reflected signals of the transmit beams;
   a processor configured to:
      calculate channel coherence for the received signals to produce one or more channel coherence images;
      calculate transmit coherence for the received signals to produce one or more transmit coherence images;
      combine information from at least one of the channel coherence images and at least one of the transmit coherence images to identify moving objects; and
      process the received signals from different transmits in overlapping regions to produce a final image compensated for the moving objects; and
   a display configured to display the final image.

14. The system of claim 13, wherein the processor is configured to calculate the channel coherence by using the received signals to which are performed one or more of the following: delaying, weighting, and phase shifting the received signals.

15. The system of claim 13, wherein the processor is configured to calculate the channel coherence with respective received signals at each sensor of the transducer.

16. The system of claim 13, wherein the processor is configured to calculate the transmit coherence using scan line data representing the overlapping region covered by the transmit beams, and the scan lines are generated by one or more of processing, weighting, delaying, phase shifting, and summing the respective received signals for use in calculating transmit coherence.

17. The system of claim 13, wherein the processor is configured to calculate:
   the channel coherence using coherence factor process comprising abs(SumChannelData/SumAbsChannelData), where "abs" is an operator for an absolute value, SumChannelData is a sum of channel data in the receive beamforming, and SumAbsChannelData is an absolute value of each of respective the channel data before doing the sum of the channel data, and
   the transmit coherence using coherence factor process comprising abs(SumTransmitData/SumAbsTransmitData), where SumTransmitData is a sum of data from the different transmits used in coherent compounding, and SumAbsTransmitData is an absolute value of each of the respective transmit data before doing the sum in the coherent compounding.

18. The system of claim 13, wherein the processor is configured to identify the moving objects by:
   generating a difference value (CFdiff) for a first portion P of an image by subtracting a corresponding first portion of the transmit coherence image (CFtx) from a corresponding first portion of the channel coherence image (CFch); and
   comparing the difference value to a threshold,
   wherein when the difference value is higher than the threshold, the first portion P of the image is considered to be a part of a moving object and set to be a compensated image Pm, and
   wherein when the difference value is not higher than the threshold, the first portion P of the image is not considered to be a part of a moving object and set to be a non-compensated image P.

19. The system of claim 18, wherein the processor is configured to generate the first portion Po using equation: Po=Pm*CFdiff+(1−CFdiff)*P, where Pm is a compensated first portion, and P is the uncompensated first portion.

20. The system of claim 13, wherein the processor is configured to use retrospect transmit beamforming to produce the one or more transmit coherence images.

* * * * *